United States Patent
Chenaux et al.

(10) Patent No.: US 10,660,658 B2
(45) Date of Patent: May 26, 2020

(54) REAMER DRIVER CONNECTION

(71) Applicant: Incipio Devices SA, St-Blaise (CH)

(72) Inventors: Fabrice Chenaux, Cortaillod (CH); André Lechot, Orvin (CH)

(73) Assignee: Incipio Devices SA, St. Blaise (CH)

( * ) Notice: Subject to any disclaimer, the term of this patent is extended or adjusted under 35 U.S.C. 154(b) by 465 days.

(21) Appl. No.: 15/355,151

(22) Filed: Nov. 18, 2016

(65) Prior Publication Data

US 2018/0153560 A1 Jun. 7, 2018

Related U.S. Application Data

(60) Provisional application No. 62/256,749, filed on Nov. 18, 2015.

(51) Int. Cl.
| | |
|---|---|
| *A61B 17/32* | (2006.01) |
| *A61B 17/56* | (2006.01) |
| *A61B 17/16* | (2006.01) |
| *A61B 50/30* | (2016.01) |

(52) U.S. Cl.
CPC ...... *A61B 17/1624* (2013.01); *A61B 17/1617* (2013.01); *A61B 17/1666* (2013.01); *A61B 50/30* (2016.02); *A61B 17/1626* (2013.01); *A61B 2050/3008* (2016.02)

(58) Field of Classification Search
CPC ............ A61B 50/30; A61B 2050/3008; A61B 17/1624; A61B 17/1617; A61B 17/1666; A61B 17/1626; B25G 1/00; B25G 1/10
USPC ........................................ 606/79–85; 81/489
See application file for complete search history.

(56) References Cited

U.S. PATENT DOCUMENTS

| | | |
|---|---|---|
| 5,658,290 A | 8/1997 | Lechot |
| 6,250,858 B1 | 6/2001 | Salyer |
| 6,540,739 B2 | 4/2003 | Lechot |
| 6,854,742 B2 | 2/2005 | Salyer et al. |
| 7,056,317 B2 | 6/2006 | Lechot |
| 7,955,320 B2 | 6/2011 | Desarzens et al. |
| 7,955,323 B2 | 6/2011 | Lechot |

(Continued)

OTHER PUBLICATIONS

International Search Report, International patent application No. PCT/IB2016/001143; dated Feb. 23, 2017.

*Primary Examiner* — Jessica Weiss
(74) *Attorney, Agent, or Firm* — Da Vinci Partners LLC; John Moetteli

(57) ABSTRACT

The invention provides a surgical tool driver having a proximal end having a coupling and a distal end comprising a surgical tool connector having a release sleeve for disconnecting the surgical tool. The surgical tool connector further includes a locking member having a locking head adapted for coupling with at least one surgical tool. The locking member is slidingly disposed and at least substantially enclosed within the center of the driver and closely interfaces therewith so as to minimize seams, gaps or openings. The locking member has an axial range of motion which assures that between an unlock and lock position, the locking head is embedded in the driver in the unlock position and then extends axially outwardly, in snug juxtaposition with the driver, to a lock position which is capable of locking a surgical tool to the tool driver in a manner so as to avoid the exposure of a significant seam, gap or opening during activation and so helping prevent debris and/or bone chips from entering the driver.

27 Claims, 8 Drawing Sheets

(56) References Cited

U.S. PATENT DOCUMENTS

| | | | |
|---|---|---|---|
| 8,323,284 B2 | 12/2012 | Ferreira | |
| 2006/0195110 A1* | 8/2006 | White | A61B 17/1666 606/81 |
| 2008/0058804 A1* | 3/2008 | Lechot | A61B 17/1631 606/53 |
| 2008/0167653 A1* | 7/2008 | Watlington | A61B 17/1615 606/81 |
| 2009/0088757 A1* | 4/2009 | Tulkis | A61B 17/1666 606/81 |
| 2009/0138016 A1* | 5/2009 | Berthusen | A61B 17/1624 606/80 |
| 2012/0022536 A1 | 1/2012 | Lualdi | |
| 2012/0023733 A1 | 2/2012 | Cannell et al. | |
| 2013/0213678 A1 | 8/2013 | Weekes | |
| 2013/0331841 A1 | 12/2013 | Roger et al. | |

* cited by examiner

REAMER DRIVER CONNECTION

CROSS REFERENCE TO RELATED APPLICATION(S)

This application claims priority to PCT Application No. PCT/IB2016/001143, filed Aug. 18, 2016, and U.S. application 62/256,749, filed 18 Nov. 2015, entitled REAMER DRIVER CONNECTION, the content of the entirety of which are explicitly incorporated herein by reference and relied upon to define features for which protection may be sought hereby as it is believed that the entirety thereof contributes to solving the technical problem underlying the invention, some features that may be mentioned hereunder being of particular importance.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

BACKGROUND OF THE INVENTION

This invention relates to systems and methods for bone cutting devices, particularly surgery tools such as acetabular reamer driver, which incorporate a mechanism to connect or release the acetabular reamer from the driver. In particular, this invention relates to tools for cutting bone, such as reamers for cutting the cotyloid cavity of the acetabulum in the event of the replacement of the hip joint by a prosthetic cup.

It is well known that such tools are complicated mechanical devices. Their complication is generally associated with having a greater number of crevasses and recesses that are difficult, if not almost impossible, to clean with ease. Devices that are not properly cleaned and sterilized contribute to the risk of disease transfer from patient to patient following the emergence of certain "prions" that are not killed by normal hospital sterilization and need to be physically removed by washing/rinsing. Such debris can be carriers for disease or infection, which is of course to be avoided.

Acetabular reamers in the prior art are generally press-formed out of stamped, flat metal stock. In a typical such case, Applicant has noticed that unnecessarily large gaps and recesses are a by-product of these fabrication methods. In addition, the mechanism for locking the surgical tool on the driver includes moving parts, which movement may present additional gaps and recesses into which blood or soft tissue can become trapped or logged in a manner that is difficult to remove, even after autoclaving.

What is needed is a surgical tool connector that prevents debris and bone chips from entering into the mechanism and potentially disconnect the surgical tool or instrument from the surgical tool driver. In addition, what is needed is a surgical tool driver which reduces soft tissue irritation while rotating by limiting the sharp edges of components located around the head of the reamer driver. Still further, what is needed is a surgical tool connector that minimizes the number of components and so minimizes the risk that parts could be inadvertently lost in a patient's body cavity.

SUMMARY OF THE INVENTION

The invention provides a surgical tool driver having a proximal end having a coupling and a distal end comprising a surgical tool connector having a release sleeve for disconnecting the surgical tool. The surgical tool connector further includes a locking member having a locking head adapted for coupling with at least one surgical tool. The locking member is slidingly disposed at the center of the driver at least partially enclosed therein and closely interfaces therewith so as to minimize seams, gaps or openings. The locking member has an axial range of motion which assures that between an unlock and lock position, the locking head is embedded in the driver in the unlock position and then extends axially outwardly, in snug juxtaposition with the driver, to a lock position which is capable of locking a surgical tool to the tool driver in a manner so as to avoid the exposure of a significant seam, gap or opening during activation and so helping prevent debris and/or bone chips from entering the driver.

It is an object of the invention to prevent debris and bone chips from entering into the mechanism and potentially disconnect the reamer from the reamer driver. It is another object of the invention to provide an easy to assemble and disassemble reamer driver connection for better cleaning and sterilization.

It is another object of the invention to minimize the number of components and to minimize the risk that parts could be lost.

It is another object of the invention to reduce soft tissue irritation while rotating by limiting the sharp edges of components located around the head of the reamer driver.

Those skilled in the art will appreciate that elements in the figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE
PREFERRED EMBODIMENT

Figure 1:
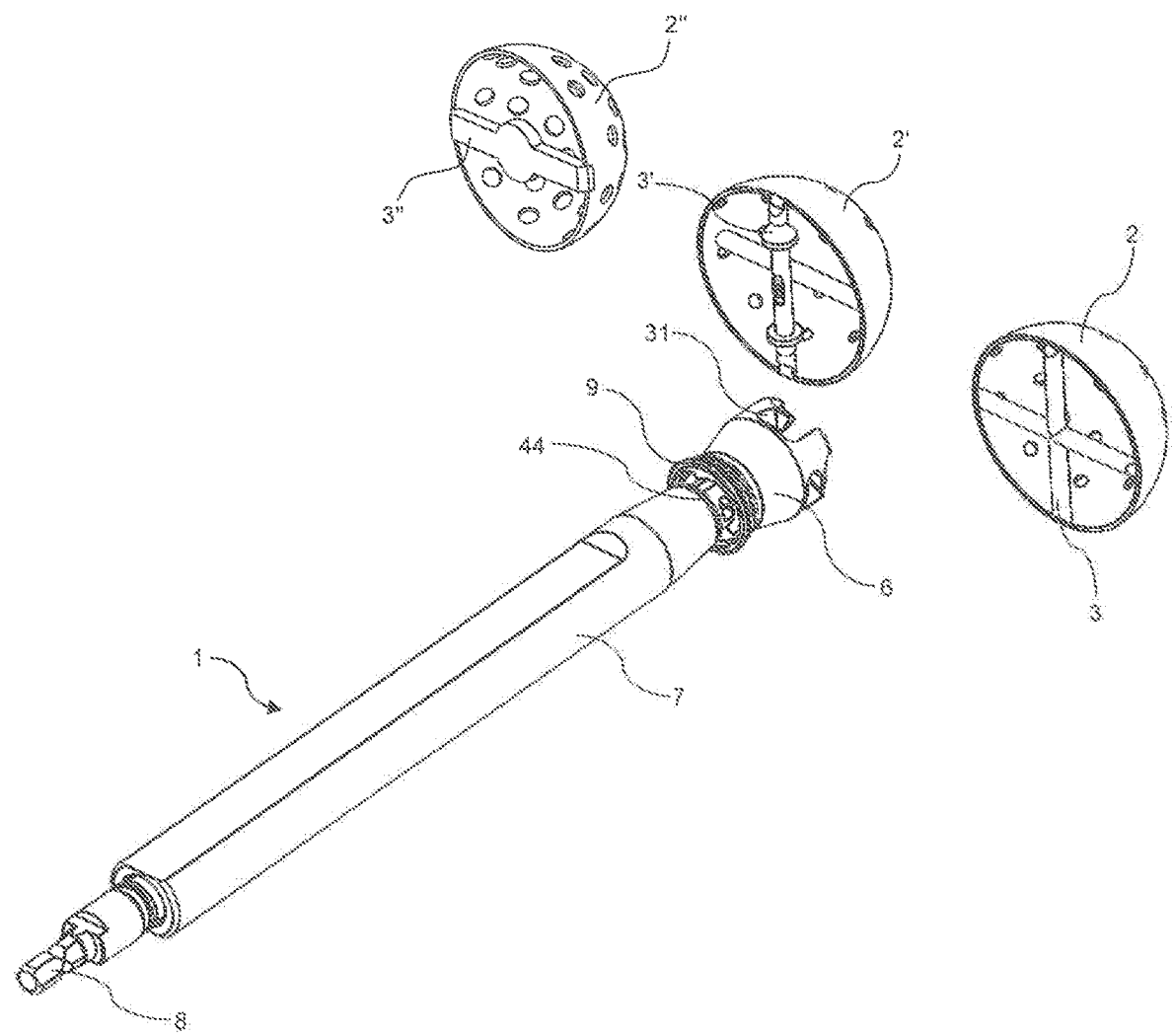
FIG. 1 is a perspective view of the preferred embodiment of the reamer driver with three acetabular reamers with different type of connector bars.

Referring to FIG. 1, a surgical tool, in this case, an acetabular reamer driver 1 is provided to assist the surgeon in reaming the acetabular socket for the implantation of a cup prosthesis. The reamer driver 1 includes a single driver head 6 that can be connected to different types of acetabular reamers 2, 2', 2". A release sleeve 9 can be pulled backward to open the connection and connect or release the acetabular reamer from the driver. The driver 1 has a driver head 6 with a stem connected to an elongated shaft 41 ending with a connector 8 that can be coupled to a source of energy (powered drill for example). An elongated grip 7, also called handle sleeve is assembled around the elongated shaft 41 and allows the surgeon to hold the reamer driver while the shaft 41 and driver head 6 is rotating. A washer 44 insures bearing contact between the handle sleeve 7 and the distal portion of the reamer driver 1.

By way of example only, three acetabular reamers 2, 2', 2", all having different coupling types, are shown. The acetabular reamer 2 has four connecting bars 3 converging at the center of the reamer to form a cross. The acetabular reamer 2' has two connecting bars 3' spaced apart and perpendicular from each other. The acetabular reamer 2" has one bar 3" with a boss at the center thereof. It will be noted that the acetabular reamer connections may have only one, two or three connecting bars not necessary oriented perpendicular to each other. The acetabular reamer may be of different shapes, such as cylindrical, conical, flat or any other profile. Other instruments or surgical tools may be connected to the tool driver in this manner—not just acetabular reamers. The shape of the bars 3, 3', 3" of the acetabular reamers 2, 2', 2" include both circular and square cross-sections but can be of any other shape or cross-section.

It should be understood that although "reamer" or "acetabular reamer" is mentioned herein as a surgical tool which interfaces with the holder of the invention, any surgical tool or instrument having a compatible interface may be driven or held by the invention.

Figure 2:
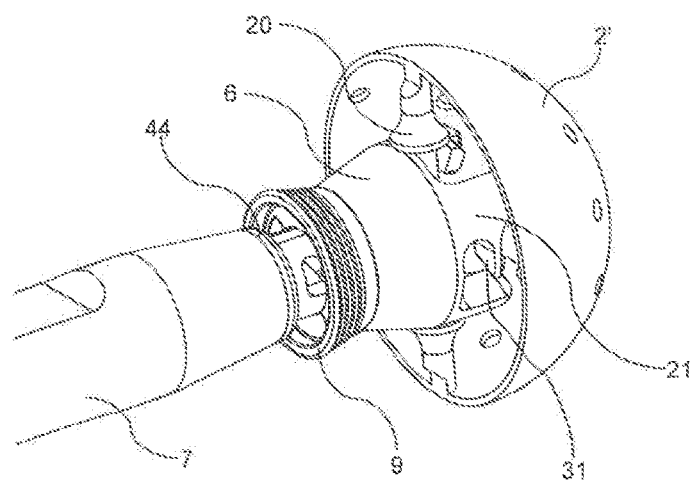
FIG. 2 is a perspective view of the preferred embodiment of the reamer driver head having an acetabular reamer connected thereto.
Figure 3:
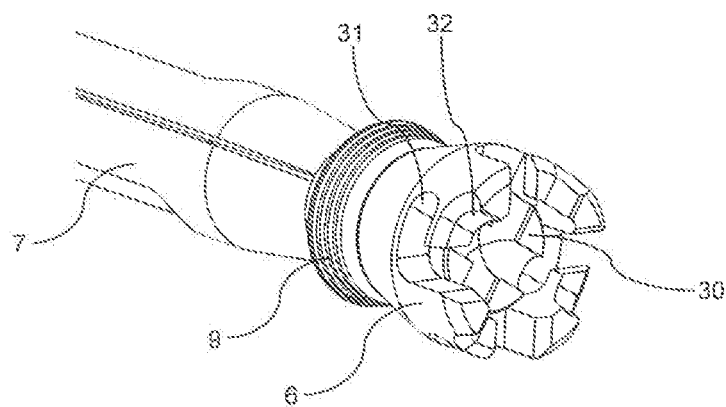
FIG. 3 is a second perspective view of the reamer driver head.

Referring now to FIG. 2, the acetabular reamer 2' is shown connected to the reamer driver 1. At least one connecting bar 3' is engaged into one L-shaped, bayonet opening 31 of the driver head 6 (shown in FIG. 3). When the acetabular reamer which is to be connected to the reamer driver 1 has spaced apart connecting bars 3', the more distal connecting bar is typically in contact with the front surface 32 of the driver head 6. Centering features 20 may be used to keep the acetabular reamer 2' centered with the cylindrical portion 21 of the driver head 6.

Figure 4:
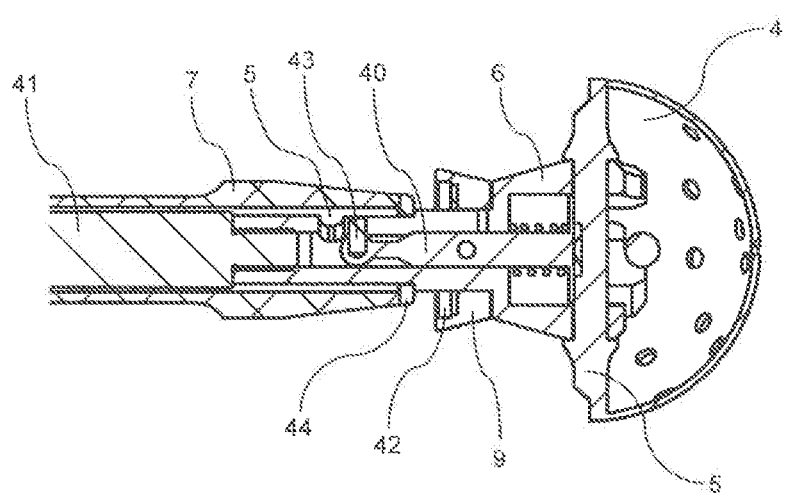
FIG. 4 is a cross-section view of the reamer driver head having an acetabular reamer connected thereto.

Now referring to FIG. 4, an axial cross-section of the reamer driver 1 is shown. A locking member 40 is slidingly, axially disposed at the center of the driver head 6 and is shown here in its locked position. The locking member 40 closely interfaces with the inner portion recess of the driver head 6 to minimize seams, gaps or opening. The locking member 40 and its locking head 30 captures the connecting bar 3' of the acetabular reamer 4 once the connecting bar 3' is engaged into the L-shaped, bayonet openings 31 and therefore maintains the reamer firmly connected to the reamer driver 1.

Figure 5A:
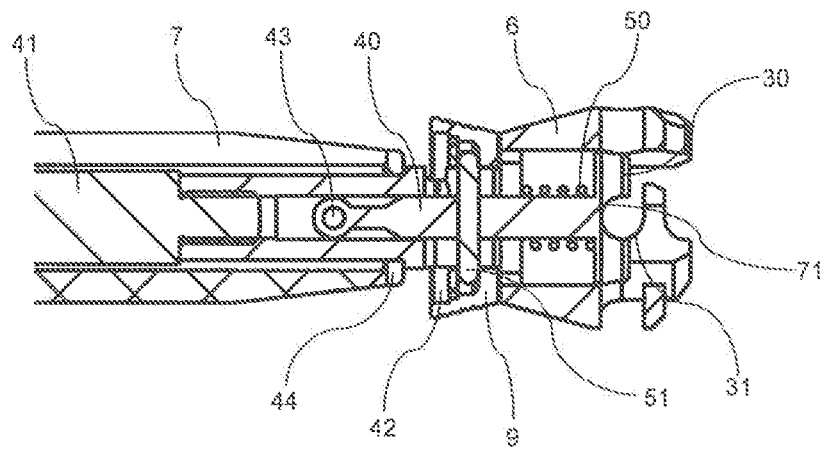
FIG. 5A is a detailed cross-section view of the reamer driver head in its closed position.
Figure 5B:
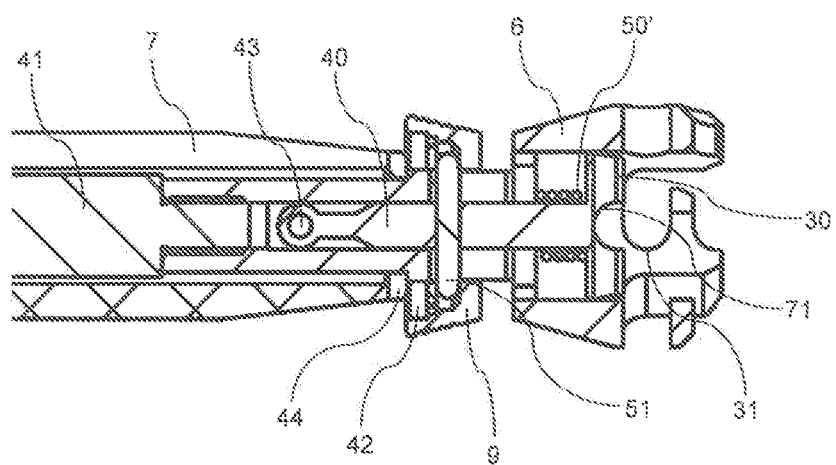
FIG. 5B is a detailed cross-section view of the reamer driver head in its opened position.
Figure 6A:
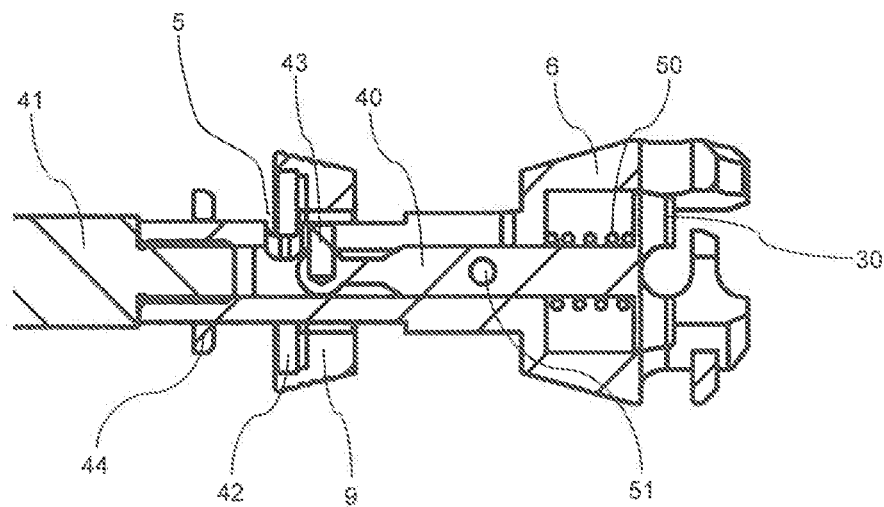
FIG. 6A is a cross-section view of the reamer driver head partially disassembled.
Figure 6B:
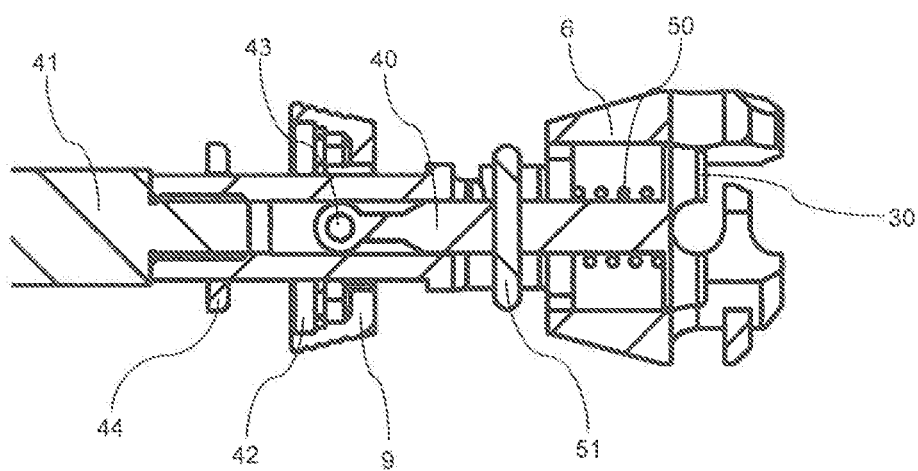
FIG. 6B is a second cross-section view of the reamer driver head partially disassembled taken perpendicular to that of FIG. 6A.

FIG. 5A is a second cross-section, perpendicular to the cross-section of FIG. 4. The locking member 40 is shown still in its locked position. At least one groove 71, located in the locking head 30 of the locking member 40, closes the L-shape opening 31 and so maintains the connecting bar of the acetabular reamer in the connected and locked position. A compression spring 50 maintains the locking member 40 in its locked position, biasing the locking member and therefore the locking head 30 against the connecting bar. A cross-pin 51, rigidly assembled (by press fit or welding for example) into the locking member 40, can be inserted and connected into the release sleeve 9 by another bayonet-like passageway 75, 76 and maintained in position by an elastic member such as a spring or spring washer 42, or ball detent (not shown) which has a simple design in which tangs 78 (shown in FIG. 7C) bias against the pin. By pulling the release sleeve 9 backward, the locking member 40 and therefore its locking head 30 move backward and clear the L-shaped opening 31, allowing the connecting bar of the acetabular reamer to be removed, as shown in the cross-section view of FIG. 5B. During this opened action, the spring 50' is compressed. In a highly useful and convenient manner, an operator may connect the surgical tool to the surgical tool driver 1 without having to manually pull on the release sleeve 9. In this embodiment, while engaging the connecting bar into the L-shaped openings 31, the connecting bar contacts the front face of the locking head 30 and therefore pushes it backward until it reaches its opened position (note that in other embodiments, instead of the front face, pins are contacted which are pushed back). This clears/opens the L-shaped opening 31 and allows the connecting bar to be fully engaged into the L-shaped opening 31. When the connecting bar is fully engaged into the end of the L-shaped opening 31, the locking head 30 is biased by the compression spring 50 into its initial locking position. The grooves 71, located in the locking head 30, close the L-shape openings 31 and block the connecting bar of the acetabular reamer in the connected position. Pulling on the release sleeve 9 to release the connecting bar is then mandatory. The locking member 40 has an axial range of motion which assures that between an unlock and lock position, the locking head 30 is embedded in the driver head 6 in the unlock position and then extends axially outwardly, in snug juxtaposition with the driver head, to a lock position which is capable of locking a surgical tool to the tool driver in a manner so as to avoid the exposure of a significant seam, gap or opening during activation and so helping prevent debris and/or bone chips from entering the driver Importantly, the locking member 40 and locking head 30 of the tool driver 1 are essentially fully contained within the envelop of the driver head 6 and intermediate shaft 72', being devoid of components that can snag or tear soft tissue during operation of the driver 1. This adds further to the comfort and security offered patients. One significant advantage of the present invention is the ability of disassembling the reamer driver for cleaning and sterilization. Referring now to FIGS. 6A and 6B, cross-section views of the reamer driver show the release sleeve 9 disconnected from the cross-pin 51. By rotating the release sleeve 9 about the stem (an intermediate shaft 72' connecting a main shaft 41 and the driver head 6) of the driver head 6, the cross-pin 51 follows the passageways 75, 76 with the spring washer 42 allowing for movement of the cross-pin 51 through this passageway 75, thus disengaging the cross-pin 51 and therefore allowing the disconnection of the two components for cleaning. The handle sleeve 7 may also be pulled off of the elongated shaft 41 for better cleaning. The inside diameter of the washer 44 is selected such that it moves freely on the shaft portion of the driver head 6 but does not fall out of the assembly, which may be attained by providing that the diameter of the shaft 41 has a smaller diameter where the washer 44 is to be retained, and a larger diameter adjacent thereto, to prevent it from sliding off (see lower left portion of FIG. 7B). In fact, the driver 1 is designed so that although all parts can be disassembled one from the other for cleaning, the parts remain loosely assembled so that no part may simply fall off and be lost.

Figure 7A:
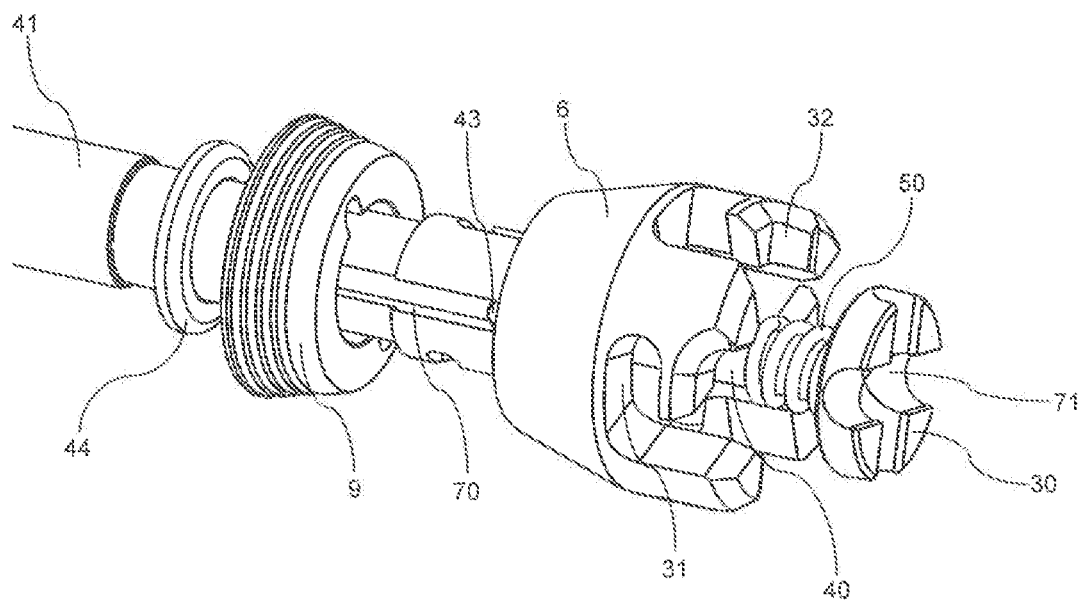
FIG. 7A is a perspective view of the reamer driver head fully disassembled.
Figure 7B:
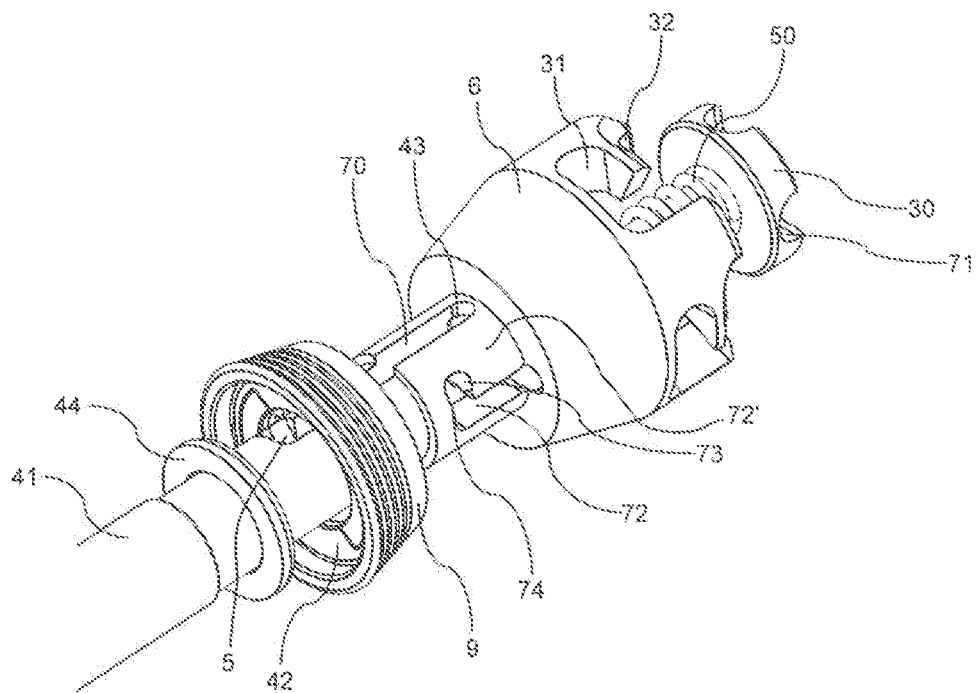
FIG. 7B is a different perspective view of the reamer driver head fully disassembled.

Referring now to FIGS. 7A and 7B, the fully disassembled (but still loosely held together) reamer driver 1 is shown. The release sleeve 9 has been disconnected from the cross-pin 51 which frees the locking member allowing the locking member 40 and its locking head 30 to freely move forward, outside the driver head 6. In this state, the pin 43 slides into the bayonet recess 70 until reaching the end of the recess distally, which prevents the locking member from falling out of the driver head 6. The proximal L-shape portion 5 of the bayonet recess provides clearance to the pin 43 when the locking member is turned into the lock open position. The locking member is maintained in a lock open position by the cross-pin 51 being engaged in the L-shape 73 of the bayonet recess 72. In other words, the retaining pin 43 is connected to the proximal end of the locking member 40. This pin 43 is captured in and slides along the groove 70 of the shaft portion of the driver head 6 and stops the locking member 40 from completely falling out of the driver head 6 due to the fact that the pin 43 hits the end of the groove 70 which prevents the locking member from completely passing through and falling out of the driver head 6. Again, this prevents medical staff from losing components during disassembling, cleaning and sterilization, representing a significant advantage for patient safety and comfort.

The groove 72 guides and limits the range of motion of the cross-pin 51 of the locking member 40, and therefore the movements of the release sleeve 9 when connected to it. By pulling the release sleeve 9 backward, the cross-pin 51 slides in the groove 72 until reaching its proximal end 74. The locking head 30 is then in its fully opened position and an acetabular reamer can be inserted into or pulled out of the driver head. If the release sleeve 9 is released from this position, the compression spring 50 will push the locking member 40 and its locking head 30 back in its initial closed position. On the other hand, when the locking member 40 and its locking head 30 are in the fully opened position, a counterclockwise rotation of the release sleeve 9 moves the cross-pin 51 towards the L-shaped end 73 of the groove 72 of the stem or immediate shaft 72' and locks the driver 1 in an open position. This position prevents the compression spring 50 from pushing the locking member 40 and its locking head 30 back in the closed position and thereby maintains the locking mechanism in this open position. This option gives the surgeon the ability to use the reamer driver in the opened position without locking the acetabular reamer to the driver which in certain surgical interventions, provides a further significant advantage.

Figure 7C:
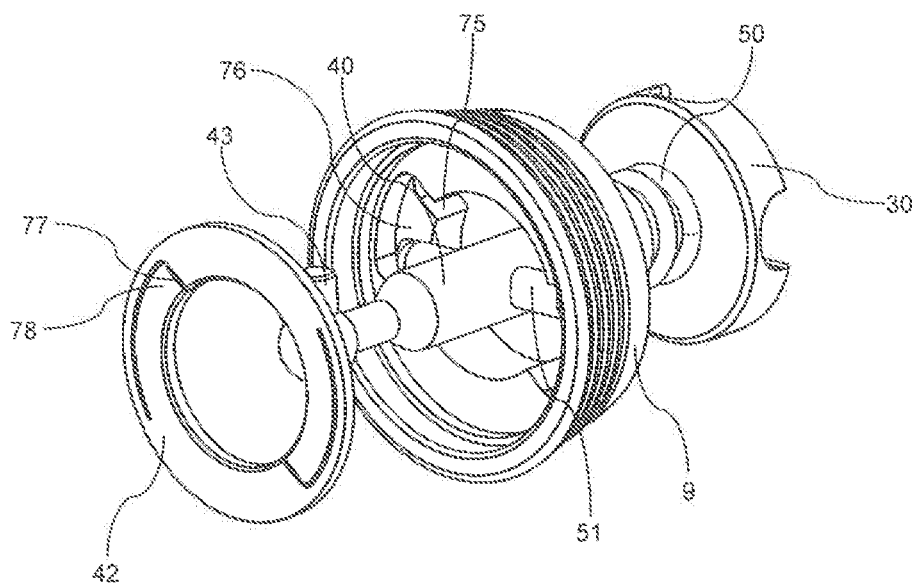
FIG. 7C is an exploded view of the release sleeve and the locking mechanism with some components removed for clarity.

Referring now to FIG. 7C, an exploded view of the release sleeve 9 is shown, minus the sleeve 7, intermediate shaft 72' and the driver head 6. These components are not shown in this figure for clarity and simplification of the drawings. The opening 75 of the release sleeve 9 allows the cross-pin 51 to be inserted into it. The spring washer 42 has a groove 77 forming a tang or elastic blade 78 which acts as a spring. After insertion of the cross-pin 51 through the opening 75, a rotation of the release sleeve 9 clockwise locks the cross-pin 51 into the channel 76. The tang 78 maintains pressure on the cross-pin 51 and avoids its free motion. The release sleeve 9 is then connected to the cross-pin 51. For disassembling, a counterclockwise rotation of the release sleeve 9 disengages the cross-pin 51 from the channel 76. The disconnection force may be adjusted by modifying, for example, the dimensions of the groove 77 forming the elastic blade 78. Different geometries of the release sleeve 9 and the spring washer 42 which allow connection and disconnection of the cross-pin may be considered without changing the scope of the present invention. In an alternate embodiment, a spring loaded ball detent (not shown) or other type of elastic members providing the same spring effect may be used in place of the spring washer 42. In still another alternate embodiment, the release sleeve 9 has a spring forceps feature (not shown) which may be used to connect and disconnect the cross-pin.

Figure 8:
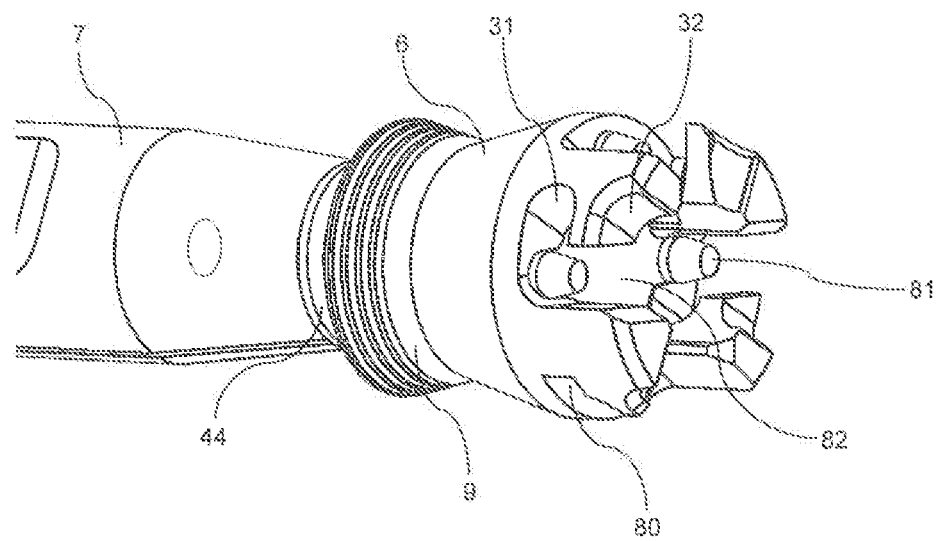
FIG. 8 is a perspective view of the second embodiment of the reamer driver head.

Now referring to FIG. 8, a second embodiment of the reamer driver is shown. The locking head 82 has at least one pin 81 located in such a way to close the L-shaped openings 31 and therefore capture the connecting bars of the surgical tool once the connecting bars engage the pins which firmly maintains the reamer firmly connected to the driver. Different L-shaped, bayonet openings 80 may be used to connect non-cylindrical connecting bars of different types of acetabular reamers. As shown is this figure, both rectangular L-shaped openings 80 and cylindrical L-shaped openings 31 are used in the same tool driver 1 in order to permit one configuration of the driver head to connect to different acetabular reamers having either rectangular or cylindrical connecting bars.

Figure 9A:
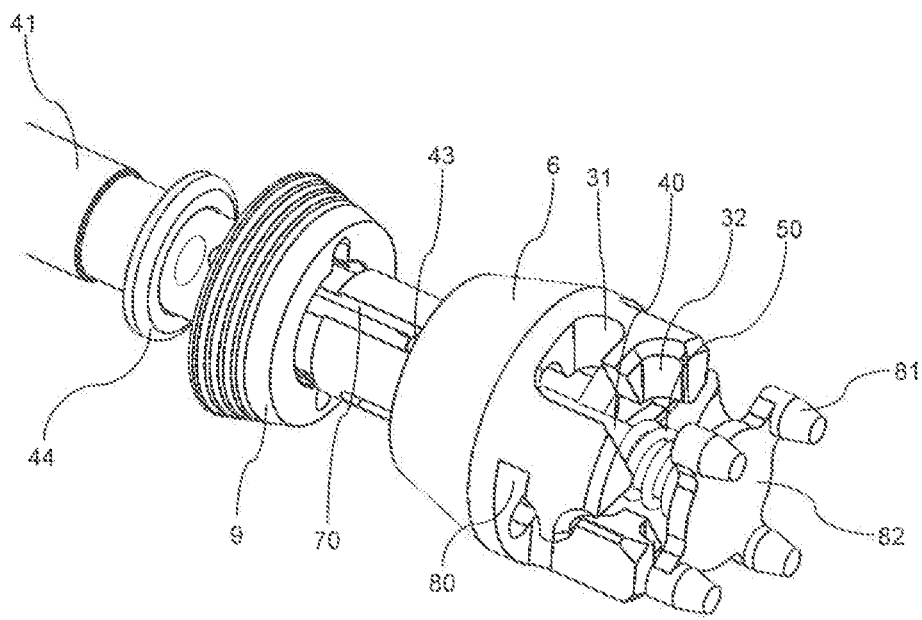
FIG. 9A is a second perspective view of the second embodiment of the reamer driver head fully disassembled.
Figure 9B:
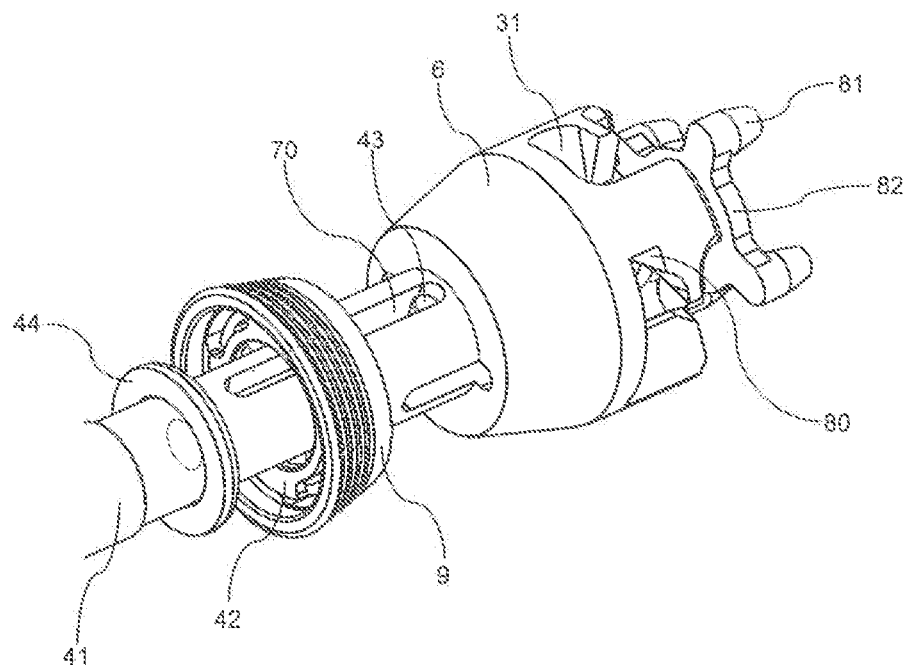
FIG. 9B is a third perspective view of a second embodiment of the reamer driver head fully disassembled.

Referring to FIGS. 9A and 9B, the second embodiment is shown in a fully disassembled state. The release sleeve 9 has been disconnected from the cross-pin 51 allowing the locking member 40 and its locking head 30 to freely move forward and outside the driver head 6. Here too, a retaining pin 43 is connected to the proximal end of the locking member 40. This pin is captured by and slides in the groove 70 of the shaft portion of the driver head 6 and stops the locking member 40 from completely falling out of the reamer driver. Note that in order to prevent gaps and openings allowing debris to enter into the mechanism, the locking head 82 (on the surface indicated by this reference number in FIG. 9B) of the locking member 40' which locking head does not have a cylindrical shape, slides within the driver head 6 in a recess having a matching shape, thereby minimizing gaps and grooves that would otherwise be receptacles for contaminants. In any case, it should be noted that a portion (whether a pin 81 or a surface 71) of the locking head 30, 82 is formed to extend beyond the driver head 6 to engage against a portion of a bar of the surgical tool and with extending axially parallel surfaces of the locking head "extruding" from the driver, in a manner similar to toothpaste being pressed out of a toothpaste tube. The engagement of this portion 81, 71 of the bar at least partially closes the bayonet passage a sufficient amount to lock the bar of the surgical tool in place.

Figure 10:
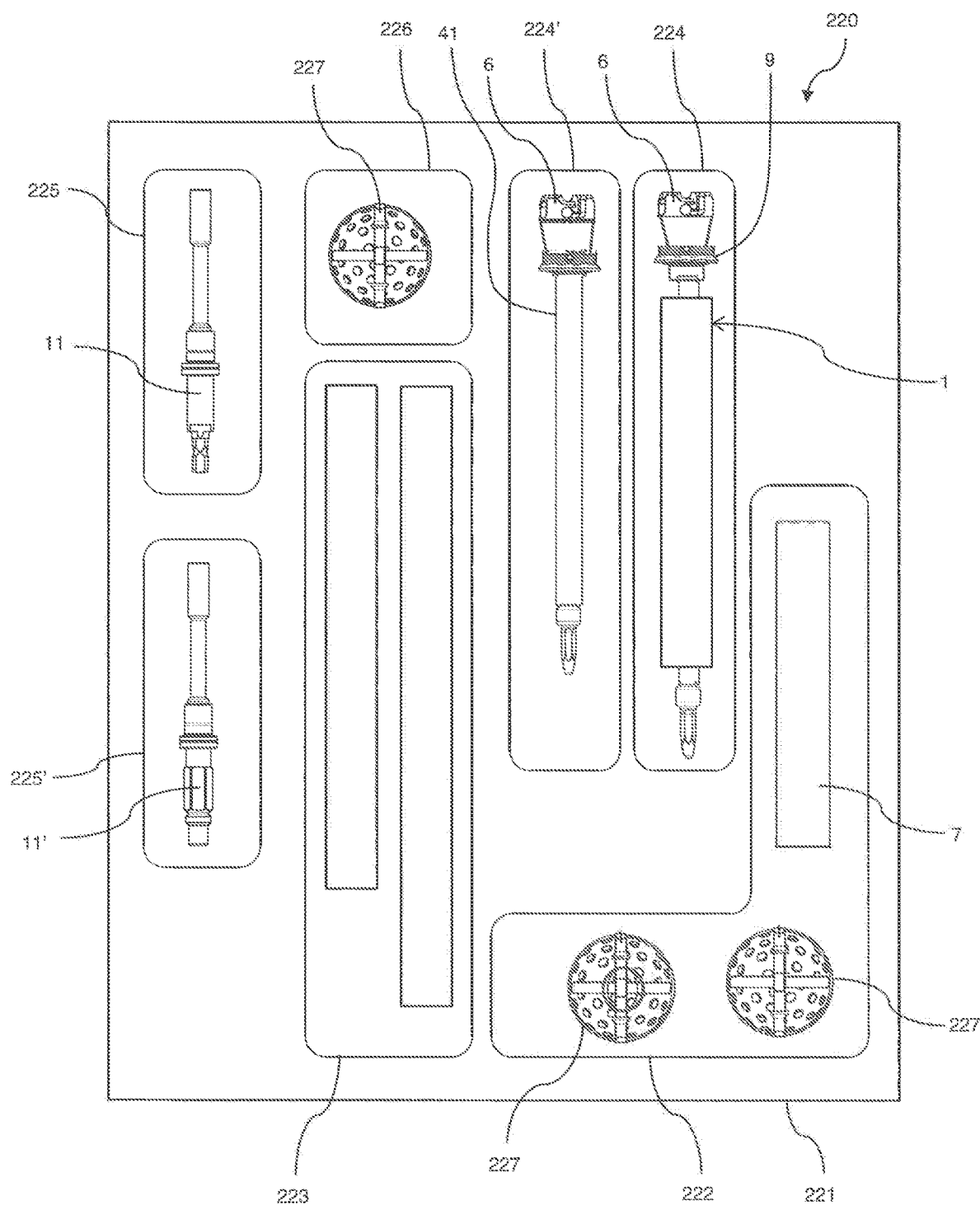
FIG. 10 is a plan view of a kit of the invention.

Referring now to FIG. 10, a kit 220 includes the surgical reamer driver 1 and its components (including some alternate components for alternate configurations), and in addition, a case 221 for organizing and storing the components of the kit. The surgical kit 220 further includes surgical tools 227 (optionally having differing outside diameters may be provided) of various sizes and styles, adapted to interface with the driver head 6 of the driver 1. Optionally, an alternative motor coupling 11, 11' are provided, having an alternative connection configuration. Such components are retained in recesses 222, 223, 224, 224', 225, 225', 226 of the case 221.

An advantage of the present invention is to provide a simple reamer driver connection that allows quick coupling of different type of acetabular reamers in which the mechanism is contained in the center of the driver. In comparison to the existing reamer driver connections described in the prior art, the locking mechanism located in the center of the driver prevent debris and bone chips to enter into the mechanism and potentially disconnect the reamer from the reamer driver.

In another advantage, the invention also reduces soft tissue irritation while rotating by limiting the sharp edges of components located around the head of the reamer driver.

Another advantage of the invention is to provide an easy to assemble and disassemble reamer driver connection for better cleaning and sterilization. The number of components and the risk that parts could be lost have been minimized.

Still further, an advantage is that sharp edges are minimized thereby reducing soft tissue irritation during use.

Importantly, a still further advantage is that the locking member and locking head of the tool driver are fully contained within the envelop of the driver head and intermediate shaft, being devoid of components that can snag or tear soft tissue during operation.

It will be understood that the particular method and devices embodying the invention are shown by way of illustration and not as a limitation of the invention. Although certain illustrative embodiments of the invention have been shown and described here, a wide range of modification, changes and substitutions is contemplated in the foregoing disclosure.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention. The patents and articles mentioned above are hereby incorporated by reference herein, unless otherwise noted, to the extent that the same are not inconsistent with this disclosure.

Other characteristics and modes of execution of the invention are described in the appended claims. Further, the invention should be considered as comprising all possible combinations of every feature described in the instant specification, appended claims, and/or drawing figures which may be considered new, inventive and industrially applicable. Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A surgical tool driver having:
a proximal end comprising a coupling;
a distal end comprising a driver head comprising a surgical tool connector and a release sleeve disposed over a shaft for disconnecting a surgical tool from the surgical tool connector, the surgical tool connector further including a locking member having a locking head comprising at least one pin and adapted for coupling with at least two surgical tool types, the locking member being slidingly disposed within the surgical tool driver and having an axial range of motion between an unlocked and a locked position, wherein the locking head is recessed within the surgical tool driver in the unlocked position and configured to extend axially outwardly from the surgical tool driver, interfacing with a complementary internal surface of the surgical tool, to the locked position for locking the surgical tool to the surgical tool driver;
wherein debris and/or bone chips are prevented from entering the surgical tool driver when the surgical tool is locked to the surgical tool driver; and
wherein the at least one pin of the locking head is configured to be axially biased and positioned with respect to a bar of the surgical tool when the bar is inserted into the surgical tool connector such that the at least one pin is configured to be pushed to an open position by the bar as the bar enters the driver head, thereby enabling installation and locking of the surgical tool into the driver head without having to manually actuate the release sleeve.

2. The surgical tool driver of claim 1, wherein the driver head is adapted to receive a surgical tool that has a bar with a boss connection.

3. The surgical tool driver of claim 1, wherein the driver head is adapted to receive a surgical tool that has a bar connection.

4. The surgical tool driver of claim 1, wherein the driver head is adapted to receive a surgical tool that has a recessed bar connection.

5. The surgical tool driver of claim 1, wherein the driver head is adapted to receive a surgical tool that has a bar connection that is cylindrical in cross section.

6. The surgical tool driver of claim 1, wherein the driver head is adapted to receive a surgical tool that has a bar that is square or rectangular in cross section.

7. The surgical tool driver of claim 1, wherein the driver head is adapted to receive a surgical tool that has a bar that has a centering feature.

8. The surgical tool driver of claim 1, wherein the shaft on which the release sleeve is disposed has a bayonet passage formed there through which guides the locking member between the unlocked position and the locked position.

9. The surgical tool driver of claim 1, wherein a compression spring biases the locking member and the locking head against a bar of the surgical tool so as to lock the surgical tool to the surgical tool driver.

10. The surgical tool driver of claim 1, wherein a cross-pin of the locking member is adapted to be inserted and connected into the release sleeve by a bayonet-like passageway and is maintained in position by an elastic member.

11. The surgical tool driver of claim 10, wherein the elastic member is a spring washer having tangs which bias the cross-pin and retain a selected position of the release sleeve.

12. The surgical tool driver of claim 1, wherein the release sleeve is configured to be pulled backward so that the locking member and its locking head move backward and clear an L-shaped opening in which the surgical tool is retained, allowing the removal of a bar of the surgical tool.

13. The surgical tool driver of claim 1, further comprising a connection bar interfacing feature adapted to engage and be pushed open and actuated by a bar of the surgical tool.

14. The surgical tool driver of claim 1, wherein the locking member interfaces with a bayonet groove of the release sleeve, permitting the locking member to be unlocked from an end-portion thereof and extended out of the driver head a set distance to facilitate cleaning and sterilization.

15. The surgical tool driver of claim 1, wherein the release sleeve releasably connects with a protrusion of the locking member in a bayonet fashion, while being retained against complete disassembly therefrom during cleaning and sterilization.

16. The surgical tool driver of claim 1, wherein a spring washer is disposed in the release sleeve, the spring washer having a groove forming a tang or elastic blade configured to act as a spring against a pin of the locking member to maintain a position selection made by an operator.

17. The surgical tool driver of claim 1, wherein an outer surface of the locking member is partially cylindrical.

18. The surgical tool driver of claim 1, wherein an outer surface of the locking member is partially square.

19. The surgical tool driver of claim 1, wherein the locking member and its locking head are fully contained within an envelope of the driver head and an intermediate shaft, being devoid of components that can snag or tear soft tissue during operation.

20. The surgical tool driver of claim 1, wherein the locking head further comprises a connection bar interfacing recess adapted to engage with and lock against the bar of the surgical tool by an interfacing bias provided by a biasing device.

21. The surgical tool driver of claim 1, wherein the locking head further comprises a connection bar interfacing pin configured to block an inserted bar of the surgical tool adapted to engage with and lock against the bar of the surgical tool by an interfacing bias provided by a biasing device.

22. The surgical tool driver of claim 1, further comprising an elongated grip and a drive enclosed in the elongated grip, wherein the surgical tool connector is located at a distal end of the elongated grip and the coupling is located at a proximal end of the elongated grip.

23. A surgical kit comprising at least one surgical tool driver as recited in claim 1, the surgical kit further comprising a case for organizing and storing the components of the surgical kit.

24. A surgical kit including at least one surgical tool driver as recited in claim 1, the surgical kit further including a plurality of surgical tools each having a different size and style adapted to interface with the surgical tool connector.

25. The surgical kit of claim 24, wherein the surgical kit further includes a motor coupling having a connection for connecting to a drive.

26. A surgical tool driver having:
a proximal end comprising a coupling;
a distal end comprising a driver head comprising a surgical tool connector and a release sleeve disposed over a shaft for disconnecting a surgical tool from the surgical tool connector, the surgical tool connector further including a locking member having a locking head comprising at least one pin and adapted for coupling with at least two surgical tool types, the locking member being slidingly disposed within the surgical tool driver and having an axial range of motion between an unlocked and a locked position, wherein the locking head is recessed within the surgical tool driver in the unlocked position and configured to move axially outwardly from the surgical tool driver, interfacing with a complementary internal surface of the surgical tool, to the locked position for locking the surgical tool to the surgical tool driver; wherein debris and/or bone chips are prevented from entering the surgical tool driver when the surgical tool is locked to the surgical tool driver; and
wherein the at least one pin of the locking head is configured to be axially biased with respect to a bar of the surgical tool as the bar is inserted into the surgical tool connector such that when the bar of the surgical tool is inserted into the driver head, the bar of the surgical tool is configured to contact the at least one pin of the locking head and push it proximally to an open position, thereby enabling installation and locking of the surgical tool into the driver head without having to manually actuate the release sleeve.

27. A surgical tool driver having:
a proximal end comprising a coupling;
a distal end comprising a driver head comprising a surgical tool connector and a release sleeve disposed over a shaft for disconnecting a surgical tool from the surgical tool connector, the surgical tool connector further including a locking member having a locking head comprising at least one groove and adapted for coupling with at least two surgical tool types, the locking member being slidingly disposed within the surgical tool driver and having an axial range of motion between an unlocked and a locked position, wherein the locking head is recessed within the surgical tool driver in the unlocked position and configured to extend axially outwardly from the surgical tool driver, interfacing with a complementary internal surface of the surgical tool, to the locked position for locking the surgical tool to the surgical tool driver;

wherein debris and/or bone chips are prevented from entering the surgical tool driver when the surgical tool is locked to the surgical tool driver; and wherein the at least one groove of the locking head is configured to be axially biased and positioned with respect to a bar of the surgical tool when the bar is inserted into the surgical tool connector such that the at least one groove closes an L-shaped opening of the driver head and maintains the bar of the surgical tool in a connected position, thereby enabling installation and locking of the surgical tool into the driver head without having to manually actuate the release sleeve.

* * * * *